United States Patent [19]

Marker et al.

[11] Patent Number: 5,571,387
[45] Date of Patent: Nov. 5, 1996

[54] CONTINUOUS SINGLE VESSEL DISTILLATION AND ADSORPTION PROCESS

[75] Inventors: Terry L. Marker, Warrenville; Santi Kulprathipanja, Inverness; Simon H. Hobbs, Chicago, all of Ill.

[73] Assignee: UOP, Des Plaines, Ill.

[21] Appl. No.: 304,919

[22] Filed: Sep. 13, 1994

[51] Int. Cl.[6] .................... B01D 15/00; B01D 3/00; C07C 41/00
[52] U.S. Cl. .................. 203/41; 203/18; 203/DIG. 6; 202/183; 568/699; 568/917
[58] Field of Search .................. 203/18, 19, 41, 203/DIG. 6, 29; 568/697, 699, 913, 917; 202/41, 183, 184

[56] References Cited

U.S. PATENT DOCUMENTS

| | | | |
|---|---|---|---|
| 2,556,248 | 6/1951 | Amick | 203/41 |
| 2,768,942 | 10/1956 | Marple | 203/41 |
| 3,122,486 | 2/1964 | Skarstrom | 202/42 |
| 4,273,621 | 6/1981 | Fornoff | 203/41 |
| 4,345,973 | 8/1982 | Ladisch et al. | 203/19 |
| 4,504,687 | 3/1985 | Jones | 203/DIG. 6 |
| 4,906,787 | 3/1960 | Huang et al. | 568/697 |
| 5,324,866 | 6/1994 | Marker et al. | 568/697 |
| 5,368,691 | 11/1994 | Asselineau et al. | 203/DIG. 6 |

OTHER PUBLICATIONS

Ming, Z. et al; *Adsorptive Distillation—Novel Hybrid Separation Process;* Progress in Natural Science; Jun. 1994, vol. 4, No. 5.

*Primary Examiner*—Robert J. Warden
*Assistant Examiner*—Christopher Kim
*Attorney, Agent, or Firm*—Thomas K. McBride; Eugene I. Snyder; Maryann Maas

[57] ABSTRACT

The present invention is a process for separating at least a first component from a second component of at least a first stream within a single vessel having at least one distillation zone and an adsorption zone. The invention may be applied to separates an alcohol from a mixture of the alcohol and water, such as separating isopropyl alcohol from a mixture of isopropyl alcohol and water. The invention may be applied to more complex systems such as separating isopropyl alcohol and separating diisopropyl ether from the effluents of each reactor of a two-stage diisopropyl ether production process. The benefit of the invention is a high purity separation process at reduced capital equipment costs.

14 Claims, 2 Drawing Sheets

CONTINUOUS SINGLE VESSEL DISTILLATION AND ADSORPTION PROCESS

FIELD OF THE INVENTION

The present invention relates to a process for separating a first component from a second component of at least one stream using both distillation and adsorption combined in a single vessel. More specifically, the present invention uses an apparatus having a distillation zone to remove at least a portion of the second component and an adsorption zone containing an adsorbent capable of selectively adsorbing at least a portion of the second component.

BACKGROUND OF THE INVENTION

In commercial distillations for the separation of one component or a plurality of components from mixtures containing the same, it is often difficult to achieve the desired degree of purity. A leading example of the difficulty of separating one component from another is the separation of an alcohol from water or from an azeotropic mixture of alcohol and water. Many approaches have been suggested for processing mixtures and azeotrope-containing streams to secure the desired separation of one component of the mixture or azeotrope from another component. In general, these operations have been relatively expensive and, in many instances, not entirely satisfactory.

U.S. Pat. No. 4,906,787 discloses a process for producing diisopropyl ether containing negligible levels of alcohol and water contaminants by first hydrating propylene in the presence of an acidic zeolite. The result of the hydration was an aqueous mixture of ether and alcohol. This aqueous mixture was then passed into a distillation unit operated at conditions effective to provide an azeotropic overhead stream containing mostly ether and only minor amounts of alcohol and water. The azeotropic overhead stream was then passed to an alcohol separation unit of an extraction column which used process feedwater as the extraction medium. Due to the extraction of alcohol from the ether-rich phase, the solubility of water in the ether-rich phase is reduced leading to further loss of water from the ether product. U.S. Pat. No. 4,906,787 also teaches that the alcohol separation unit can be in the form of a decanter with the condensed azeotropic overhead stream separating into an ether enriched upper phase and an aqueous alcohol enriched lower phase.

U.S. Pat. No. 4,345,973 discloses the recovery of ethanol from a fermentation broth by distilling a dilute aqueous alcohol to its azeotrope, distilling the azeotropic mixture using a third component of either an organic solvent or a strong salt solution to break the azeotrope and remove the remaining water, and distilling the resulting mixture to separate water from this third component.

U.S. Pat. No. 3,122,486 discloses a process of using a distillation unit followed by an absorption unit. An alcohol and water mixture was first distilled into a water stream and an alcohol and water distillate stream. The alcohol and water stream was then introduced to an adsorption unit which contained a molecular sieve or ion exchange resin capable of selectively adsorbing water. As the stream containing isopropanol and water moved through the adsorbent, water was adsorbed and removed. A dry alcohol stream was the product removed from the adsorption zone. U.S. Pat. No. 3,122,486 also teaches the use of a swing bed adsorption system that allowed for one bed to continuously remove water from the distillate while the other bed was being desorbed. The water-saturated adsorbent bed was isolated through using a specific valving arrangement in order to provide suction to the bed, thereby removing water vapor from the bed. Once the pressure in the bed undergoing desorption reaches a predetermined low point, a portion of the dry alcohol product from the other adsorption bed that is undergoing adsorption is passed through the bed for backwashing, thereby preparing the bed undergoing desorption to be switched to adsorption.

The two-stage diisopropyl ether (DIPE) production process disclosed in U.S. Pat. No. 5,324,866 teaches that two separation units were required to separate an isopropyl alcohol (IPA) and water mixture, and to separate a DIPE, IPA, and water mixture. The first separation unit was a fractionation unit which separated an IPA and water mixture into a water stream and an IPA stream that also contained some water. The second separation unit was also a fractionation unit and the IPA and water stream from the first separation unit, and an IPA, DIPE and water mixture were separated into a largely DIPE stream and a largely IPA stream.

Applicants are the first to address the need for a process to separate a first component from a second component, e.g., water and an alcohol, by combining the physical separation processes of distillation and adsorption within a single vessel. As discussed above, others have proposed processes which use both a distillation unit and an adsorption unit, or two distillation units. But applicants here have redefined the economics of such two-unit processes since, with applicants' invention, the prior art two-unit systems are no longer necessary, and only one unit is required to carry out the same functions. A significant reduction in capital equipment costs is now possible since, with applicants' invention, one process vessel is eliminated.

SUMMARY OF THE INVENTION

The purpose of the present invention is to provide a process of separating at least a first component from a second component in a first stream using both distillation and adsorption in a single vessel. The process of the present invention may be performed by (1) distilling in the distillation zone at least a portion of the first stream into a second stream enriched in the first component and a third stream enriched in the second component; (2) conducting the second stream to the adsorption zone and selectively adsorbing the second component from the second stream to afford a second component-depleted fourth stream; and (3) collecting the fourth stream from the adsorption zone.

Alternatively, the vessel may have two distillation zones and one adsorption zone, in which case the process may be performed by (1) distilling in the first distillation zone the first stream into a second stream enriched in the first component and a third stream enriched in the second component; (2) conducting the second stream to the adsorption zone and selectively adsorbing a portion of the second component from the second stream to afford a fourth stream depleted in the second component; (3) passing the fourth stream to the second distillation zone and distilling the fourth stream into a fifth stream containing at least 98 mass % first component and a sixth stream; and (4) collecting the fifth stream from the second distillation zone.

A specific embodiment of the invention is a process for separating IPA from a stream containing IPA and water using a single vessel having a distillation zone and an adsorption zone where the invention is performed by (1) distilling the stream containing IPA and water in the distillation zone into a stream enriched in IPA and a stream enriched in water; (2) conducting the stream enriched in IPA to the adsorption zone and selectively adsorbing water to afford a stream containing at least 98 mass % IPA; (3) collecting the stream containing at least 98 mass % from the adsorption zone.

Another specific embodiment is one where IPA is separated from a stream containing IPA and water in a single vessel having a first distillation zone, an adsorption zone positioned above the first distillation zone containing an adsorbent capable of adsorbing water, and a second distillation zone positioned above the adsorption zone where the invention is performed by (1) distilling in the first distillation zone the stream containing IPA and water into a stream enriched in IPA and a stream enriched in water; (2) conducting the stream enriched in IPA to the adsorption zone and selectively adsorbing water to afford a stream containing at least 95 mass % IPA; (3) passing the stream containing at least 95 mass % IPA to the second distillation zone and distilling to form a stream containing at least 98 mass % IPA and an IPA and water azeotrope stream; and (4) collecting the stream containing at least 98 mass % IPA from the second distillation zone.

Still another specific embodiment of the invention is one where IPA and DIPE are separated from the effluents of each reactor of a two-stage DIPE production process using a single vessel having a first distillation zone, an adsorption zone positioned above the first distillation zone containing an adsorbent capable of selectively adsorbing water, and a second distillation zone positioned above the adsorption zone. The process of the invention involves (1) distilling a stream containing IPA and water in the first distillation zone into a stream enriched in IPA and a stream enriched in water; (2) conducting the stream enriched in IPA to the adsorption zone and selectively adsorbing a portion of the water to afford a stream enriched in IPA and depleted in water; (3) passing the stream enriched in IPA and depleted in water to the second distillation zone and distilling to form a stream containing at least 98 mass % IPA, and a stream containing at least 90 mass % DIPE; and (4) collecting the stream containing at least 98 mass % IPA and the stream containing at least 90 mass % DIPE from the second distillation zone.

DETAILED DESCRIPTION OF THE INVENTION

Figure 1:
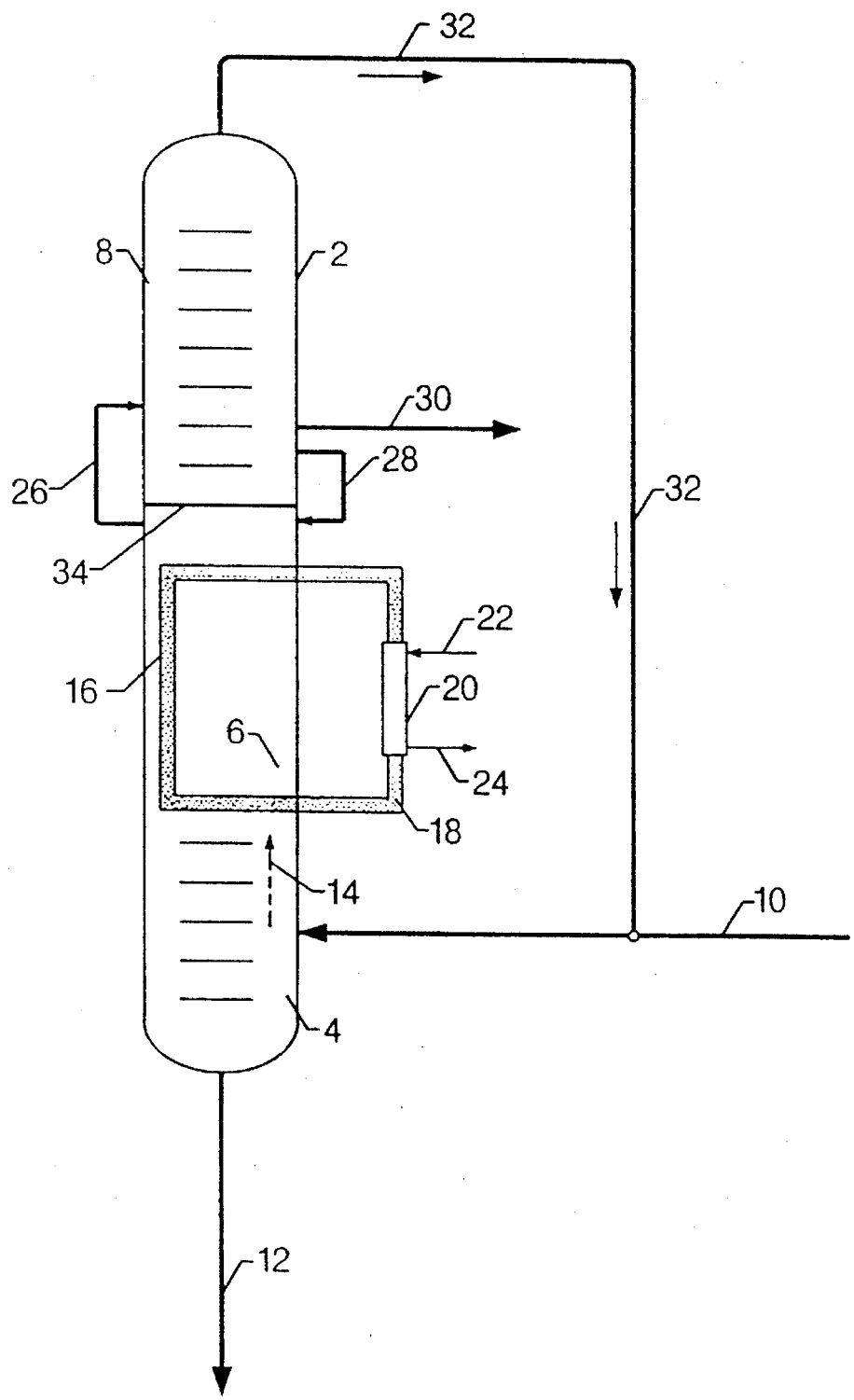
FIG. 1 is a schematic representation of a specific embodiment of the invention where IPA is separated from a stream containing IPA and water using a vessel having a first distillation zone, adsorption zone, a second distillation zone, and a regeneration zone.

The present invention is a process for separating at least a first component from a second component of a stream in a single vessel having at least one distillation zone and an adsorption zone. Typically the zones are physically arranged within the vessel so that the adsorption zone is positioned above the distillation zone. Furthermore, in a preferred embodiment, the apparatus used in the process of the present invention is a cylindrical vessel consisting of a first distillation zone, an adsorption zone positioned above the first distillation zone, and a second distillation zone positioned above the adsorption zone.

In the distillation zones, components are separated by fractionation. For example, a first stream may be separated by fractionation into a second stream enriched in the first component and a third stream enriched in the second component. The operating conditions for the distillation zones will vary depending on the relative composition of the streams and the desired first component purity. The distillation zone may contain trays, plates, and packing to assist in the separation. The distillation zone may also contain catalyst for separating the first component from the second component and/or reacting the first component to form a third component.

The absorption zone contains an adsorbent that is capable of selectively adsorbing the second component. Suitable adsorbents include, but are not limited to, molecular sieves and ion exchange resins. The molecular sieve can be a naturally-occurring aluminosilicate, synthetic aluminosilicate, borosilicate, or gallosilicate. A hydrophilic molecular sieve having pore diameters large enough to adsorb most of the molecular species of the feedstock based on molecular size configurations is preferred, such as zeolite A, zeolite X, and zeolite Y. Other crystalline microporous materials such as aluminophosphates and silicoaluminophosphates can also be used. Suitable ion exchange resins include Dowex 50 or 50W, Amberlite 120, and the like. Which adsorbent is preferred depends upon the specific component to be adsorbed.

In a preferred embodiment, the adsorbent is placed in specially designed downcomers made of metal mesh screen which will allow for intimate contact of the adsorbent and the second component of the second stream. An example of a suitable system for handling the adsorbent in the adsorption zone can be found in U.S. Pat. No. 5,108,550 which is herein incorporated by reference. Spent adsorbent may be periodically or continuously removed from the adsorption zone and passed to a regeneration zone positioned external to the vessel. In the regeneration zone, spent adsorbent is contacted with a heated noncondensible purge gas to desorb at least a portion of the second component from of the spent adsorbent. The adsorbent is then passed to the adsorption zone for reuse in adsorbing the second component from the second stream. A stream containing the second component that was desorbed from the adsorbent is removed from the regeneration zone. As an option, the adsorption zone may also be operated in the pressure swing bed mode.

In its simplest form, the invention involves (1) distilling in the distillation zone at least a portion of the first stream into a second stream enriched in the first component and a third stream enriched in the second component; and (2) conducting the second stream to the adsorption zone and selectively adsorbing at least a portion of the second component from the second stream to afford a fourth stream depleted in the second component. The stream to be separated by the present invention can be any stream which contains two components. For example, the stream could be a mixture of an alcohol such as ethanol, isopropyl alcohol, n-propyl alcohol, sec-butyl alcohol, or cyclohexanol, and water, a mixture of phenol and water, or a mixture of pyridine and water. Each component can be made of a single constituent or a plurality of constituents. The invention is best explained in terms of the specific embodiment where the stream to be separated is a mixture of IPA and water with the first component being the IPA and the second component being the water. Typically, the IPA and water mixture will be the effluent from an IPA production process, and the water will be present in an excess amount. Commonly expected concentrations are, for example, 82 mass % water and 18 mass % IPA. The present invention, by requiring only a single vessel, significantly reduces both capital costs and operational costs of the separation incurred in separating IPA and water as compared with the two-unit systems, usually an azeotrope column and a distillation column, currently used in industry.

The stream containing the IPA and water mixture is introduced into the distillation zone where a majority of the water is easily separated by fractionation and removed from the IPA due to the difference in boiling points of the water and the alcohol. As the concentration of water in the mixture decreases, an azeotrope of 88 mass % IPA and 12 mass % water will form and additional water will not be separated from the azeotrope in the distillation zone. The mixture then encounters the adsorption zone where additional water may be adsorbed by the adsorbent causing the concentration of water to fall below that required to maintain the azeotrope. In this embodiment, the adsorbent zone is operated so that sufficient water is adsorbed and removed to result in a stream containing at least 98 mass % IPA which is then collected. The adsorbent may be continuously regenerated as described above.

Adsorbing sufficient water to provide a stream of 98 mass % IPA may require a large amount of adsorbent and/or a high volume regeneration zone. The adsorbent and its regeneration may be costly, and a more economical embodiment of the invention is one where only a portion of the water available is removed in the adsorbent zone, and a second distillation zone is employed to separate any alcohol and water azeotrope from the alcohol. In general terms, the embodiment involves (1) distilling in the first distillation zone a first stream into a second stream enriched in a first component and a third stream enriched in a second component; (2) conducting the second stream to the adsorption zone and selectively adsorbing a portion of the second component from the second stream to afford a fourth stream depleted in the second component; (3) passing the fourth stream to the second distillation zone and distilling to form a fifth stream containing at least 98 mass % first component and a sixth stream; and (4) collecting the fifth stream from the second distillation zone.

As applied to the specific embodiment where the stream to be separated is a mixture of IPA and water with the first component being the alcohol and the second component being the water, the invention would proceed as follows. The stream containing the IPA and water mixture is introduced into the distillation zone where a majority of the water is easily separated and removed from the IPA due to the difference in boiling points of the water and the alcohol. As the concentration of water in the mixture decreases, an azeotrope of 88 mass % IPA and 12 mass % water will form, and additional water will not be separated from the azeotrope in the distillation zone. The mixture then encounters the adsorption zone where additional water may be adsorbed by the adsorbent causing the concentration of water to fall below that required to maintain the azeotrope. In this embodiment, the adsorption zone is operated so that only a portion of the available water is adsorbed and removed resulting in a stream requiring further distillation. The adsorbent may be continuously regenerated as described above, but since in this embodiment less water is being adsorbed, the adsorbent and its regeneration costs will be reduced. The water-depleted stream is then introduced to a second distillation zone where IPA may be separated from the IPA and water azeotrope that reforms with the removal of IPA due to the slight yet sufficient difference in the boiling points of the alcohol and the azeotrope. A stream of at least 98 mass % IPA may be collected, and the stream containing the azeotrope may be recycled to the first distillation zone.

Applicants have found that when using the two distillation zone embodiment, it is preferred that the vessel have a physical barrier between the adsorbent zone and the second distillation zone. The effluent from the adsorbent zone is conducted in a line external to the vessel and is introduced to the second distillation zone at least a short distance from the beginning of the second distillation zone. For example, when the distillation zone is comprised of a series of trays, the adsorbent zone effluent should be introduced at least two trays into the second distillation zone. The stream containing substantially the first component is withdrawn from the second distillation zone in the portion of the second distillation zone after the beginning of the second desorbent zone and before the introduction of the adsorbent zone effluent. Since the adsorbent effluent is introduced at a point after the withdrawal of the first component stream, there is less opportunity for mixing, and the concentration of the first component in the first component stream is higher. Of course, a conduit allowing for non-removed liquid to pass to the adsorption column may be provided.

The embodiment where the vessel contains a first distillation zone, an adsorbent zone, and a second distillation zone can also be applied to the more complex situation of separating DIPE, IPA, and water from the effluents of each reactor of two-stage DIPE production processes. Generally, the first stage of a DIPE production process is the hydration of propylene to form IPA and the second stage is the etherification of the IPA with propylene to form DIPE. The effluent from the first stage after unreacted propylene is removed is a mixture of IPA and water, but it is desirable to pass only the IPA to the second stage. The effluent from the second stage after unreacted propylene is removed is a mixture of IPA and DIPE, but it is desirable to separate the DIPE as the product and recycle the IPA. To achieve these separations, prior art systems such as U.S. Pat. No. 5,324,866 feed the first stage effluent to a water recovery unit to separate out a majority of the water in the effluent and then feed the water-depleted first stage effluent along with the second stage effluent to a distillation column to separate IPA from an IPA-water-DIPE azeotrope which readily separates into a DIPE phase and a water phase. The present invention replaces the water recovery unit and the distillation unit of the prior art with one single vessel to which both the first and second stage effluents may be fed after removal of propylene. The propylene-containing DIPE production process feed stream, suitable hydration and etherification catalysts, and operating conditions for DIPE production processes are discussed in detail in U.S. Pat. No. 5,324,866, and U.S. Ser. No. 08/079,768 which are incorporated by reference.

The specific embodiment of the invention to separate DIPE and IPA generated in two-stage DIPE production processes is performed as follows. The first stage effluent containing the IPA and water mixture is introduced into the distillation zone where a majority of the water is easily separated and removed from the IPA due to the difference in boiling points of the water and the alcohol. As the concentration of water in the mixture decreases an azeotrope of 88 mass % IPA and 12 mass % water will form, and additional water will not be separated from the azeotrope in the distillation zone. The IPA-enriched mixture then encounters the adsorption zone where additional water may be adsorbed by the adsorbent causing the concentration of water to fall below that required to maintain the azeotrope. The adsorbent may be continuously regenerated as described above. The water-depleted IPA stream is then introduced to a second distillation zone and the second stage effluent containing a mixture of DIPE and IPA is also introduced. In the second distillation zone, a 4 mass % IPA-5 mass % water-91 mass % DIPE azeotrope will form which is readily separated from IPA due to the significant difference between the boiling points of the azeotrope and the alcohol. It is important to note that in this embodiment, the adsorbent zone is operated so that only a portion of the available water is adsorbed and removed; sufficient water must be allowed to pass to the second distillation zone in order to form an IPA-water-DIPE azeotrope. Two streams are withdrawn from the second distillation zone, an IPA-water-DIPE azeotrope stream and an IPA stream. The IPA-water-DIPE azeotrope then readily separates into a 95 mass % DIPE phase and a 94 mass % water phase. The IPA stream and the 95 mass % DIPE streams are collected. The preferences discussed above regarding the physical barrier between the adsorption zone and the second distillation zone and the removal of the IPA stream prior to the introduction of the adsorption zone and the second stage effluents also apply in this specific embodiment.

The present invention may be applied to an alternate two-stage DIPE production process where the first stage is the etherification of IPA with propylene to form DIPE, and the second stage is the hydration of a portion of the DIPE product to form IPA which is recycled to the first stage. Suitable process feedstocks, and etherification and hydration catalysts are discussed in U.S. Pat. No. 5,324,866, and U.S. Ser. No. 08/079,768 which are incorporated by reference. The effluent from the first stage after unreacted propylene is removed is a mixture of DIPE and IPA, but it is desirable to separate the DIPE as the product, pass a portion of the DIPE product to the second stage, and recycle the IPA to the first stage. The effluent from the second stage after unreacted propylene is removed is a mixture of mainly IPA and water, but it is desirable to recycle only the IPA to the first stage and to separate the DIPE as a product. It is readily apparent that the present invention would perform in this application in the same manner as described above except, in this application, the first stage effluent, a mixture of DIPE and IPA, is introduced into the second distillation zone, and the second stage effluent, a mixture of water and IPA, is introduced into the first distillation zone.

Without intending any limitation on the scope of the present invention and as merely illustrative, this invention is explained below in specific terms as applied to two specific embodiments of the invention. First, the invention is explained as applied to the separation of IPA and water from a mixture of the two. Second, the invention is explained as applied to the separation of IPA and DIPE from the effluents of each reactor in a two-stage DIPE production process. For ease of understanding, the process of the invention described below is limited to the preferred embodiment of having two distillation zones and one adsorption zone. The necessary apparatus is first described and then the process of the invention as applied to the embodiment is discussed.

Referring now to FIG. 1, the vessel 2 contains three zones. The first zone is first distillation zone 4 and is made up of a series of distillation trays. The second zone is adsorption zone 6 which contains a downcomer arrangement 16 having disposed therein a molecular sieve suitable for selectively adsorbing water indicated at 18. Downcomer arrangement 16 is also in fluid communication with regeneration zone 20, which is located outside the vessel. The third zone is second distillation zone 8 which is made up of a series of distillation trays. Second distillation zone 8 is separated from adsorption zone 6 by a physical barrier 34.

The 18 mass % IPA and 82 mass % water mixture to be separated is introduced to the vessel through line 10 at a point within first distillation zone 4. A majority of the water, with its higher boiling point, is easily separated from the IPA and is withdrawn in line 12. It is expected that the stream in line 12 will be 99 mass % water. The remaining IPA-enriched stream, in the form of an 88 mass % IPA-12 mass % water azeotrope, is conducted to adsorption zone 6 as indicated by line 14. In adsorption zone 6, additional water is selectively adsorbed by molecular sieve adsorbent 18 so that the IPA-enriched stream is now, for example, 94 mass % IPA and 6 mass % water. Spent adsorbent is continuously removed from adsorption zone 6 via downcomer arrangement 16 and passed through regeneration zone 20 where adsorbed water is removed by passing nitrogen, heated to about 500° F., into regeneration zone 20 via line 22. A mixture of nitrogen and water exit regeneration zone 20 through line 24. Once the adsorption capacity of the molecular sieve adsorbent is restored, it is cooled (not shown) and passed from regeneration zone 20 to adsorption zone 6 via downcomer arrangement 16.

The water-depleted IPA-enriched stream (94 mass % IPA and 6 mass % water) is conducted from adsorption zone 6 to second distillation zone 8 around the physical barrier 28 via line 26. Line 26 introduces the stream at a point at least two trays from the beginning of second distillation zone 8. In second distillation zone 8, IPA is separated from the mixture by fractionation and as the concentration of IPA in the mixture decreases, the IPA-water azeotrope is once again formed. A stream of at least 98 mass % IPA is removed from second distillation zone 8 in line 30. Note that the point at which the 98 mass % IPA stream is removed is between the beginning of second distillation zone 8 and the introduction of line 26. The IPA-water azeotrope is removed from second distillation zone 8 via line 32 which is combined with line 10. Line 28 is provided to allow excess liquid to pass to adsorption zone 6.

Figure 2:
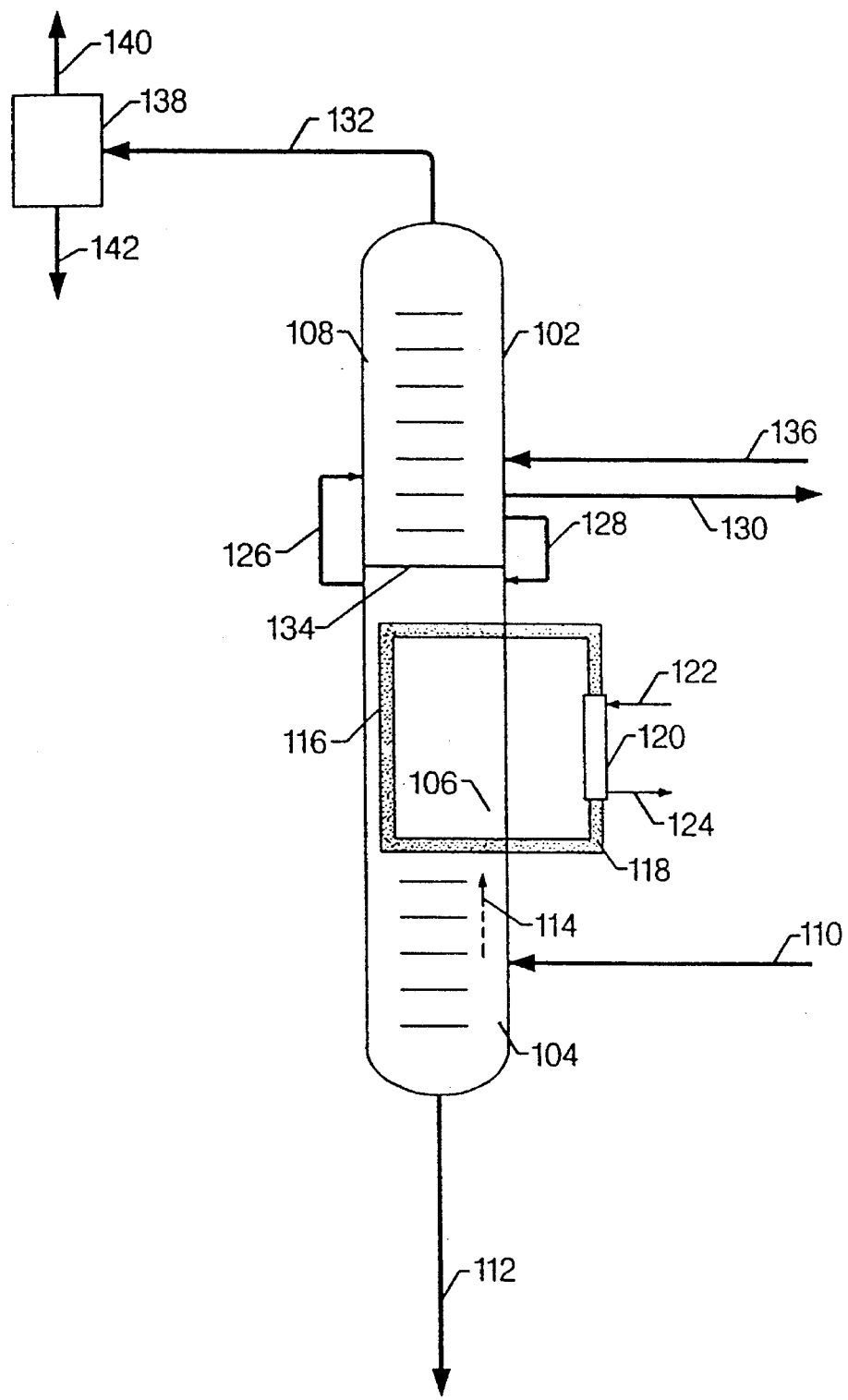
FIG. 2 is a schematic representation of a specific embodiment of the invention where IPA and DIPE are separated from two streams, one containing IPA and water, and one containing DIPE and IPA using a vessel having a first distillation zone, adsorption zone, a second distillation zone, and a regeneration zone.

The specific embodiment of separating IPA and DIPE from reactor effluents of a two-stage DIPE production process is illustrated in FIG. 2. Additional process steps between the reactors of the DIPE production process and the subject invention, such as the removal of propylene, have been omitted as they are not necessary to the illustration of the invention. The physical apparatus of the vessel is similar to the example above. The vessel 102 contains three zones. The first zone is first distillation zone 104 and is made up of a series of distillation trays. The second zone is adsorption zone 106 which contains a downcomer arrangement 116 having disposed therein a molecular sieve suitable for selectively adsorbing water indicated at 118. Downcomer arrangement 116 is also in fluid communication with regeneration zone 120 which is located outside the vessel. The third zone is second distillation zone 108 which is made up of a series of distillation trays. Second distillation zone 108 is separated from adsorption zone 106 by a physical barrier 134.

The 18 mass % IPA and 82 mass % water effluent from one reactor of the two-stage DIPE production process is introduced to the vessel through line 110 at a point within first distillation zone 104. A majority of the water, with its higher boiling point, is easily separated from the IPA and is withdrawn in line 112. It is expected that the stream in line 112 will be 99 mass % water. The remaining IPA-enriched stream, in the form of an 88 mass % IPA-12 mass % water azeotrope, is conducted to adsorption zone 106 as indicated by line 114. In adsorption zone 106, additional water is selectively adsorbed by molecular sieve adsorbent 118 so that the IPA-enriched stream is now, for example, 94 mass % IPA and 6 mass % water. Spent adsorbent is continuously removed from adsorption zone 106 via downcomer arrangement 116 and passed through regeneration zone 120 where adsorbed water is removed by passing nitrogen, heated to about 500° F., into regeneration zone 120 via line 122. A mixture of nitrogen and water exit regeneration zone 120 through line 124. Once the adsorption capacity of the molecular sieve adsorbent is restored, it is cooled (not shown) and passed from regeneration zone 120 to adsorption zone 106 via downcomer arrangement 116.

The water-depleted IPA-enriched stream (94 mass % IPA and 6 mass % water) is conducted from adsorption zone 106 to second distillation zone 108 around the physical barrier 128 via line 126. Line 126 introduces the stream at a point at least two trays from the beginning of second distillation zone 108. The 25 mass % IPA and 75 mass % DIPE effluent from the other reactor of the two-stage DIPE production process is introduced to the vessel through line 136 at a point between the beginning of distillation zone 108 and the introduction of the stream in line 126. In second distillation zone 108, IPA is separated from the mixture by fractionation and, as the concentration of IPA in the mixture decreases, a 4 mass % IPA-5 mass % water-91 mass % DIPE azeotrope is formed. A stream of at least 98 mass % IPA is removed from second distillation zone 108 in line 130. Note that the point at which the 98 mass % IPA stream is removed is between the beginning of second distillation zone 108 and the introduction of line 136. Line 128 is provided to allow excess liquid to pass to adsorption zone 106. The IPA-water-DIPE azeotrope is removed from second distillation zone 108 via line 132 and is introduced to a separator 138 where it readily separates into two phases, a 95 mass % DIPE phase and a 94 mass % water phase. The 95 mass % DIPE phase is removed from separator 138 in line 140, and the 94 mass % water phase is removed from separator 138 in line 142.

What is claimed is:

1. A process for separating in a single vessel two components present in at least a first stream comprising:

(a) providing a single vessel having a first distillation zone devoid of an adsorbent, an adsorption zone positioned above said first distillation zone and containing an adsorbent capable of selectively adsorbing the second component, and a second distillation zone devoid of an adsorbent and positioned above said adsorption zone;

(b) conducting said first stream into said first distillation zone;

(c) fractionating said first stream in said first distillation zone to afford a first distillate enriched in a first component and a first bottoms enriched in a second component;

(d) conducting said first distillate to the adsorption zone and selectively adsorbing a portion of the second component to afford a second stream depleted in the second component;

(e) passing the second stream to the second distillation zone and fractionating to afford a second distillate enriched in the first component and a second bottoms; and (f) collecting the second distillate from the second distillation zone.

2. The process of claim 1 where the sixth stream is recycled to combine with the first stream.

3. The process of claim 1 where the fifth stream contains at least 95 mass % of the first component.

4. The process of claim 1 further comprising introducing a seventh stream to the second distillation zone.

5. The process of claim 4 where the seventh stream contains an alcohol and an ether.

6. The process of claim 1 wherein the first component is an alcohol and the second component is water.

7. The process of claim 6 wherein the alcohol is selected from the group consisting of ethanol, isopropyl alcohol, n-propyl alcohol, sec-butyl alcohol, and cyclohexanol.

8. The process of claim 1 wherein at least one distillation zone contains a catalyst for reactive distillation.

9. The process of claim 1 further comprising passing at least a portion of the adsorbent to a regeneration zone positioned external to the vessel, desorbing at least a portion of the second component from the adsorbent, and recycling adsorbent from the regeneration zone to the adsorption zone.

10. The process of claim 1 further comprising where the adsorption zone is operated in a pressure swing bed mode.

11. A process for separating in a single vessel isopropyl alcohol present in a stream containing isopropyl alcohol and water comprising:

(a) providing a single vessel having a first distillation zone devoid of an adsorbent, an adsorption zone positioned above the first distillation zone containing an adsorbent capable of selectively adsorbing water, and a second distillation zone devoid of an adsorbent positioned above the adsorption zone;

(b) conducting the stream containing isopropyl alcohol and water into said first distillation zone;

(c) fractionating said stream containing isopropyl alcohol and water in the first distillation zone to afford a first distillate enriched in isopropyl alcohol and a bottoms enriched in water;

(d) conducting the first distillate enriched in isopropyl alcohol to the adsorption zone and selectively adsorbing a portion of the water to afford an isopropyl alcohol enriched water-depleted stream;

(e) passing at least a portion of the isopropyl alcohol enriched water-depleted stream to the second distillation zone and fractionating to separate a second distillate containing at least 98 mass % isopropyl alcohol, and an isopropyl alcohol and water azeotrope stream; and (f) collecting second distillate containing 98 mass % isopropyl alcohol.

12. The process of claim 11 further comprising passing at least a portion of the adsorbent to a regeneration zone positioned external to the vessel and desorbing at least a portion of the adsorbed water from the adsorbent and recycling the adsorbent from the regeneration zone to the adsorption zone.

13. A process for separating in a single vessel isopropyl alcohol and diisopropyl ether from the effluents of each reactor of a two-stage diisopropyl ether production process comprising:

(a) providing a single vessel having a first distillation zone devoid of an adsorbent, an adsorption zone positioned above the first distillation zone containing an adsorbent capable of selectively adsorbing water, and a second distillation zone devoid of an adsorbent and positioned above the adsorption zone;

(b) conducting a first reactor effluent containing isopropyl alcohol and water into the first distillation zone;

(c) fractionating said first reactor effluent containing isopropyl alcohol and water in the first distillation zone to afford a first distillate enriched in isopropyl alcohol and a bottoms enriched in water;

(d) conducting the first distillate enriched in isopropyl alcohol to the adsorption zone and selectively adsorbing a portion of the water to afford an isopropyl alcohol enriched water-depleted stream;

(e) passing at least a portion of the isopropyl alcohol enriched water-depleted stream and conducting a second reactor effluent containing diisopropyl ether, isopropyl alcohol and water to the second distillation zone and fractionating to afford an at least 98 mass % isopropyl alcohol second distillate and an at least 90 mass % diisopropyl ether third distillate; and (f) collecting the 98 mass % isopropyl alcohol second distillate and the 90 mass % diisopropyl ether third distillate.

14. The process of claim 13 further comprising passing at least a portion of the adsorbent to a regeneration zone positioned external to the vessel and desorbing at least a portion of the adsorbed water from the adsorbent and recycling the adsorbent from the regeneration zone to the adsorption zone.

* * * * *